US00PP23439P2

(12) United States Plant Patent
Kleinwee

(10) Patent No.: US PP23,439 P2
(45) Date of Patent: Feb. 26, 2013

(54) *BIDENS* PLANT NAMED 'BIDZ0001'

(50) Latin Name: *Bidens ferulifolia*
Varietal Denomination: BIDZ0001

(75) Inventor: Theodorus Cornelis Maria van Kleinwee, Enkhuizen (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 13/317,198

(22) Filed: Oct. 11, 2011

(51) Int. Cl.
*A01H 5/00* (2006.01)

(52) U.S. Cl. ..... Plt./410

(58) Field of Classification Search ..... Plt./410
See application file for complete search history.

*Primary Examiner* — Annette Para
(74) *Attorney, Agent, or Firm* — Joshua L. Price

(57) ABSTRACT

A new *Bidens* plant named 'BIDZ0001' and particularly distinguished by the bright yellow, single-type flowers, deep green foliage, free branching, medium sized and semi-upright and mounding to later becoming more of a creeping plant habit.

1 Drawing Sheet

Latin name of the genus and species of the plant claimed: *Bidens ferulifolia*.

Varietal denomination: 'BIDZ0001'.

BACKGROUND OF THE NEW PLANT

The present invention comprises a new *Bidens* plant, botanically known as *Bidens ferulifolia* and hereinafter referred to by the variety name 'BIDZ0001'.

'BIDZ0001' is a product of a planned breeding program. The new cultivar has bright yellow, single-type flowers, deep green foliage, free branching, medium sized and semi-upright and mounding to later becoming more of a creeping plant habit.

'BIDZ0001' originated from an open pollinated hybridization made in the summer of 2006 in a controlled breeding environment in Enkhuizen, The Netherlands. The female parent was the unpatented, proprietary plant designated 'F0158-1', having somewhat smaller yellow flowers of a slightly deeper hue, and more vigorous growth habit.

The male parent of 'BIDZ0001' was an unknown plant. The resultant seeds were sown in March 2007. 'BIDZ0001' was selected as one flowering plant within the progeny in May 2007.

The first act of asexual reproduction of 'BIDZ0001' was accomplished when vegetative cuttings were propagated from the initial selection in the early summer of 2007, in a controlled environment in Enkhuizen, Netherlands.

BRIEF SUMMARY OF INVENTION

Horticultural examination of plant grown from cuttings of the plant initiated in the spring of 2008 continuing thereafter, has demonstrated that the combination of characteristics as herein disclosed for 'BIDZ0001 ' are firmly fixed and are retained through successive generations of asexual reproduction.

'BIDZ0001' has not been observed under all possible environmental conditions. The phenotype may vary significantly with variations in environment such as temperature, light intensity and day length.

Plant Breeder's Rights for this cultivar were applied for in Canada on Dec. 24, 2010, #10-7134 and with CPVO on Oct. 15, 2010, #2010/2180. 'BIDZ0001' has not been made publicly available more than one year prior to the filing of this application.

The following traits have been repeatedly observed and are determined to be basic characteristics of the new variety. The combination of these characteristics distinguishes this *Bidens* as a new and distinct variety.

BRIEF DESCRIPTION OF THE PHOTOGRAPHS

The accompanying photographic drawing shows typical flower and foliage characteristics of 'BIDZ0001, with colors being as true as possible with an illustration of this type.

Figure 1:
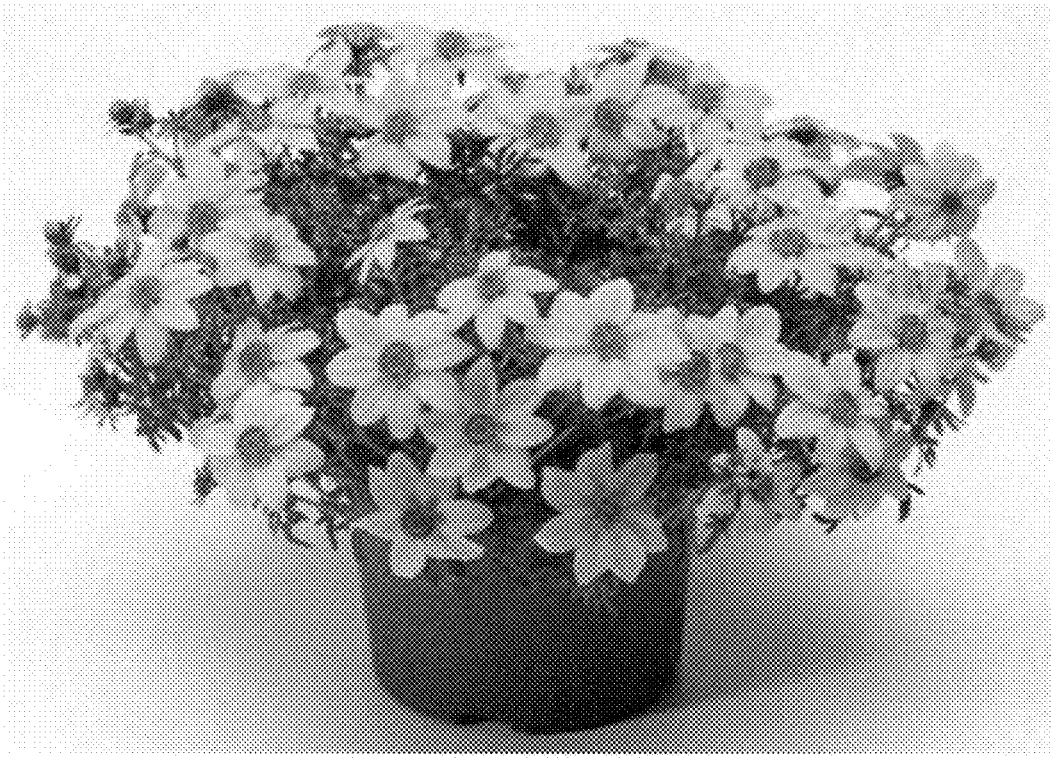
Figure 2:
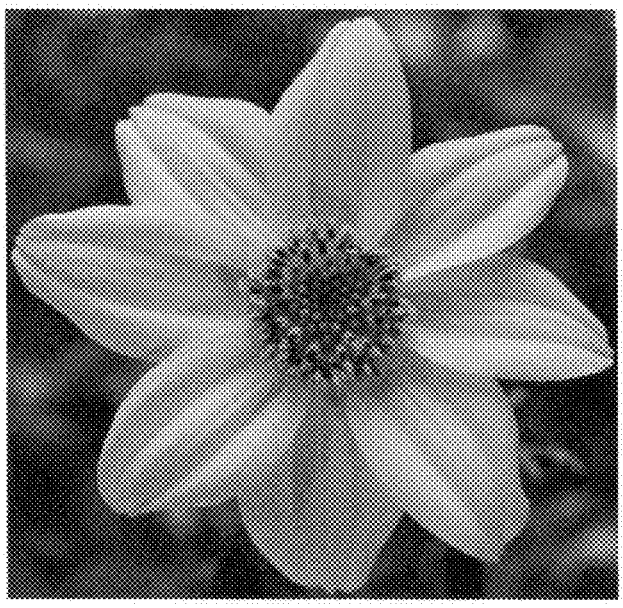

The photographic drawing shows in FIG. 1. a flowering plant of the new variety and in FIG. 2. a close-up of the flowers.

DETAILED BOTANICAL DESCRIPTION

The aforementioned photographs were taken in mid June 2010, from plants grown in a greenhouse trial in Enkhuizen, The Netherlands. These plants were growing in 12 cm pots and were approximately 16 weeks of age.

The plant descriptions and measurements were taken in September 2011 in Enkhuizen, The Netherlands, on about 7 month-old plants growing in an field trial. These plants were initially grown in the greenhouse at moderately warm temperatures and transplanted outside in mid to late May.

Color references are made to The Royal Horticultural Society Colour Chart (R.H.S.) 2001.

TABLE 1

DIFFERENCES BETWEEN THE NEW VARIETY 'BIDZ0001' AND A SIMILAR VARIETY:

| | 'BIDZ0001' | 'Fisbimex' |
|---|---|---|
| Peduncles length | Shorter | Longer |
| Flower diameter in greenhouse: | 5.5-6.0 cm | 4.5-4.8 cm |
| Plant growth habit | Medium vigor | Vigorous |

Plant:

*Form, growth and habit*.—Initially semi-upright and mounding, to later becoming more of a creeping plant habit that is freely branched with still a relatively tight plant structure.

*Plant height*.—17.0-19.0 cm.

*Plant height* (*inflorescence included*).—23.0-25.0 cm.

*Plant spread* (*base of branches to tip*).—About 34.0 cm.

Roots:

*Number of days to initiate and produce roots*.—About 12-14 days at about 24 degrees C.

*Type*.—Fine, fibrous, free branching.

*Color*.—RHS N155B but whiter.

Foliage:

*Arrangement*.—Opposite, decussate.

*Immature, leaf color, upper surface*.—Between RHS 138A.

*Lower surface*.—RHS 139C.

*Mature, leaf color, upper surface*.—RHS 137A to RHS 137B.

*Lower surface*.—RHS 138B.

*Length*.—2.3 cm.

*Width*.—1.5-2.0 cm.

*Shape*.—Deltoide, pinnatisect.

*Base shape*.—Acute to obtuse.

*Apex shape*.—Acute.

*Margin*.—Deeply incised.

*Texture, upper surface*.—Smooth, glabrous.

*Lower surface*.—Glabrous.

*Venation pattern*.—Pinnate.

*Color of veins, upper surface*.—RHS 138B.

*Color of veins, lower surface*.—RHS 138A.

*Petiole*.—

*Petiole color*.—RHS 147C to RHS 147D; with RHS 138B on the under side.

*Length*.—0.2-1.0 cm.

*Diameter*.—0.1 cm.

*Texture*.—Hirtellous.

Stem:

*Characteristics*.—Side branches develop potentially at every node.

*Color of stem*.—RHS 146C, overlaid with anthocyanin blotches of RHS N186C.

*Length of stem*.—Approximately 24.0-30.0 cm.

*Diameter*.—0.2 cm.

*Length of internodes*.—3.0-4.0 cm.

*Texture*.—Hirtellous.

Peduncle:

*Color of peduncle*.—RHS 146C, to RHS 147A closer to the inflorescence.

*Length of peduncle*.—Most often between 2.0-4.0 cm.

*Peduncle diameter*.—0.1 cm.

*Texture*.—Hirtellous.

Inflorescence:

*Type*.—Solitary inflorescences, terminal, composite type. Inflorescences positioned above the foliage on moderately strong peduncles. Inflorescences face upright.

*Blooming habit*.—Continuous flowering from spring through fall; free flowering through all weather.

*Quantity of inflorescences per plant*.—25-45.

*Lastingness of individual blooms on the plant*.—About 7-8 days, depending on temperature.

*Fragrance*.—Weak, honey smell.

Bud (just when starting to show color):

*Color*.—RHS N200A with the top and some traces of N144A.

*Length*.—0.4 cm.

*Width*.—0.4 cm.

*Shape*.—Ovate.

Immature inflorescence:

*Immature color, upper surface*.—RHS 12A.

*Lower surface*.—RHS 9A.

Mature inflorescence:

*Inflorescence horizontal diameter*.—5.6-6.0 cm in greenhouse, diminishing in size through the summer.

*Inflorescence depth*.—0.9 cm.

*'Disc' diameter*.—1.4-1.5 cm.

*Receptacle diameter*.—1.2 cm.

*Receptacle height*.—0.7 cm.

*Receptacle shape*.—Semi-spherical.

Ray florets:

*Quantity of ray florets per inflorescence*.—Usually eight, arranged in a single whorl.

*Color, upper surface*.—RHS 12A.

*Lower surface*.—RHS 9A.

*Floret width*.—1.1-1.4 cm.

*Floret length*.—1.9-2.1 cm.

*Shape*.—Oblong to elliptical.

*Base*.—Fused.

*Apex shape*.—Mostly slightly praemorse.

*Margin*.—Entire.

*Texture, upper surface*.—Smooth and glabrous.

*Lower surface*.—Smooth and glabrous.

Disc florets:

*Quantity of disc florets per inflorescence*.—About 30 to 40.

*Immature, color*.—About RHS 197A at the apex to RHS 157A basally.

*Mature, color*.—RHS 7C to RHS 2C with a apex of RHS N200A.

*Length*.—About 0.6 cm.

*Diameter*.—About 0.1 cm.

*Shape*.—Tubular.

*Apex*.—Dentate.

Phyllaries:

*Quantity per inflorescence*.—About 8 to 10 in two whorls.

*Color, upper surface*.—RHS N199A for the upper row, RHS 137C for the lowest row.

*Color, lower surface*.—RHS 199A for the upper row, RHS 137A for the lowest row.

*Length*.—About 0.5 cm.

*Width*.—About 0.15 cm for the lower row, 0.2 cm for the upper row.

*Shape*.—Ligulate.

*Apex*.—Apiculate for the upper one. Acute for the lower row.

*Base*.—Fused.

*Margin*.—Entire.

*Texture, upper surface*.—Smooth, glabrous.

*Texture, lower surface*.—Pubescent.

Reproductive organs:

*Gynoecium*.—Pistil: One. Pistil length: About 0.8 cm. Stigma shape: Cleft; reflexed. Stigma color: Close to 13B. Style length: About 0.4 cm. Ovary color: Close to RHS 157D.

*Androecium*.—Quantity per disc floret: One. Anther length: About 0.4-0.5 cm. Anther color: Closest to RHS 200A. Pollen amount: Moderate. Pollen color: Close to RHS 13A.

*Seed set*.—Quantity of seeds per inflorescence: About 25. Seed Length: About 0.5 cm. Seed Diameter: About 0.1 cm. Seed Color: Mainly RHS 202A.

Disease/pest resistance: Disease/pest resistance has not been observed on this hybrid.

What is claimed is:

1. A new and distinct variety of *Bidens* plant named 'BIDZ0001' substantially as illustrated and described herein.

* * * * *